United States Patent
Bhatt et al.

(10) Patent No.: US 9,662,394 B2
(45) Date of Patent: May 30, 2017

(54) STABILIZED EFINACONAZOLE COMPOSITIONS

(71) Applicant: Dow Pharmaceutical Sciences, Inc., Petaluma, CA (US)

(72) Inventors: Varsha Bhatt, San Francisco, CA (US); Nayan Desai, Santa Rosa, CA (US); Radhakrishnan Pillai, Santa Rosa, CA (US)

(73) Assignee: Dow Pharmaceutical Sciences, Inc., Petaluma, CA (US)

( * ) Notice: Subject to any disclaimer, the term of this patent is extended or adjusted under 35 U.S.C. 154(b) by 0 days.

(21) Appl. No.: 14/505,379

(22) Filed: Oct. 2, 2014

(65) Prior Publication Data

US 2015/0099785 A1   Apr. 9, 2015

Related U.S. Application Data

(60) Provisional application No. 61/922,867, filed on Jan. 1, 2014, provisional application No. 61/886,569, filed on Oct. 3, 2013.

(51) Int. Cl.
| | |
|---|---|
| *A61K 47/18* | (2017.01) |
| *A61K 31/454* | (2006.01) |
| *A61K 47/10* | (2017.01) |
| *A61K 47/12* | (2006.01) |
| *A61K 9/00* | (2006.01) |
| *A61K 9/06* | (2006.01) |
| *A61K 9/08* | (2006.01) |

(52) U.S. Cl.
CPC .......... *A61K 47/183* (2013.01); *A61K 9/0014* (2013.01); *A61K 9/06* (2013.01); *A61K 9/08* (2013.01); *A61K 31/454* (2013.01); *A61K 47/10* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 4,457,938 A | | 7/1984 | von Bittera |
| 4,912,124 A | | 3/1990 | Das |
| 5,208,257 A | * | 5/1993 | Kabara .......... 514/552 |
| 5,461,068 A | | 10/1995 | Thaler |
| 5,696,105 A | | 12/1997 | Hackler |
| 5,696,164 A | * | 12/1997 | Sun et al. .......... 514/562 |
| 5,814,305 A | | 9/1998 | Laugier |
| 5,874,069 A | | 2/1999 | Mendolia |
| 6,165,484 A | * | 12/2000 | Raad et al. .......... 424/405 |
| 6,197,305 B1 | | 3/2001 | Friedman |
| 6,231,875 B1 | | 5/2001 | Sun |
| 6,538,039 B2 | | 3/2003 | Laurent |
| 6,585,963 B1 | | 7/2003 | Quan |
| 6,676,953 B2 | | 1/2004 | Hexamer |
| 6,740,326 B1 | | 5/2004 | Meyer |
| 6,846,837 B2 | | 1/2005 | Maibach |
| 7,214,506 B2 | | 5/2007 | Tatsumi |
| 7,622,844 B1 | | 11/2009 | Kuhlmann-Wilsdorf |
| 8,039,494 B1 | | 10/2011 | Winckle et al. |
| 8,486,978 B2 | | 7/2013 | Winckle et al. |
| 2003/0007939 A1 | | 1/2003 | Murad |
| 2003/0082129 A1 | | 5/2003 | Buckingham |
| 2004/0180025 A1 | | 9/2004 | Long |
| 2005/0186161 A1 | | 8/2005 | Kawase |
| 2005/0244342 A1 | | 11/2005 | Friedman |
| 2006/0110415 A1 | | 5/2006 | Gupta |
| 2006/0147383 A1 | | 7/2006 | Mallard |
| 2006/0280706 A1 | | 12/2006 | Sebillotte-Arnaud |
| 2007/0041910 A1 | | 2/2007 | Pitre |
| 2007/0071705 A1 | | 3/2007 | De Oliveira |
| 2007/0082375 A1 | | 4/2007 | Tatsumi et al. |
| 2007/0142317 A1 | | 6/2007 | Warren et al. |
| 2007/0207222 A1 | | 9/2007 | Yu et al. |
| 2009/0175810 A1 | * | 7/2009 | Winckle et al. .......... 424/61 |
| 2010/0298394 A1 | | 11/2010 | Steiner et al. |
| 2010/0317695 A1 | * | 12/2010 | Okumura et al. .......... 514/326 |
| 2012/0010246 A1 | | 1/2012 | Winckle et al. |
| 2013/0064872 A1 | * | 3/2013 | Jung et al. .......... 424/401 |
| 2013/0150586 A1 | | 6/2013 | Mimura et al. |
| 2014/0228403 A1 | | 8/2014 | Winckle et al. |

FOREIGN PATENT DOCUMENTS

| | | |
|---|---|---|
| GB | 2407496 | 10/2003 |
| KR | WO2011/045765 | * 11/2011 |
| WO | 87/02580 | 5/1987 |
| WO | 99/49835 | 10/1999 |
| WO | 2004/021968 A2 | 3/2004 |
| WO | 2004/084826 | 10/2004 |
| WO | 2011/064558 A2 | 6/2011 |
| WO | 2013/130666 A1 | 9/2013 |

OTHER PUBLICATIONS

Ogura et al. In Chemical & Pharmaceutical Bulletin 47(10), 1417-1425 (1999).*
Jo Slu et al. Antimicrobial Agents and Chemotherapy 57(4), 1610-1616 (2013).*
Jannsen Pharmaceuticals, "Pevaryl®" (Mar. 2009), 3 pages.
Tatsumi et al., Therapeutic efficacy of topically applied KP-103 against experimental Tinea Unguium in Guinea Pigs in comparison with Amorolfine and Terbinafine, Antimicrobial Agents and Chemotherapy, vol. 46, No. 12, pp. 3797-3801 (Dec. 2002).
Vanderdonckt et al., Miconazole alcoholic solution in the treatment of mycotic nail infections, Mykosen, 19(17):251-256 (Sep. 1975).

* cited by examiner

*Primary Examiner* — Dennis Heyer
(74) *Attorney, Agent, or Firm* — Kilpatrick Townsend & Stockton LLP (57) ABSTRACT

The present invention provides compositions containing efinaconazole, butylated hydroxytoluene, a salt of ethylenediaminetetraacetic acid, and optional citric acid. The compositions exhibit stable color profiles and are useful in the treatment of fungal infections.

16 Claims, 2 Drawing Sheets

STABILIZED EFINACONAZOLE COMPOSITIONS

CROSS REFERENCES TO RELATED APPLICATIONS

The present application claims priority to U.S. Provisional Patent Application No. 61/886,569, filed on Oct. 3, 2013, and U.S. Provisional Patent Application No. 61/922,867, filed on Jan. 1, 2014, which applications are incorporated herein by reference in their entirety.

BACKGROUND OF THE INVENTION

Triazole anti-fungal compounds, such as ketoconazole, itraconazole, and fluconazole are known and have been the subject of scientific study, pharmaceutical development, and medical use. Although compounds in this class often exhibit antifungal activity, they differ in terms of efficacy and usefulness in different types of pharmaceutical formulations and treatments. Efinaconazole (CAS registry number 164650-44-6) is a triazole that has demonstrated activity in the treatment of onychomycosis. Formulations useful for the topical delivery of efinaconazole in the treatment of onychomycosis and other triazole antifungal drugs have been described in, e.g., U.S. Pat. No. 8,486,978. Some formulations containing triazole active ingredients exhibit varying degrees of instability during storage. Certain formulations are known to discolor within storage periods as short as one or two days, resulting in composition colors ranging from yellow to deep red or brown. Such discoloration can discourage the prescribed use of the compositions by patients who are reluctant to self-administer the discolored compositions. Stabilized formulations of triazoles such as efinaconazole are therefore needed. The present invention addresses this need.

SUMMARY OF THE INVENTION

In a first aspect, the invention provides a liquid or semisolid composition containing about 0.5% to about 15% efinaconazole by weight, butylated hydroxytoluene (BHT), and a salt of ethylenediaminetetraacetic acid (EDTA). The amounts of BHT and the salt of EDTA are sufficient to ensure the composition is: (i) colorless upon initial formulation, and (ii) colorless or pale yellow after storage for at least three weeks at a temperature of at least about 40° C. In some embodiments, the composition is colorless or pale yellow after storage for one month at a temperature of about 65° C.

In some embodiments, the amount of efinaconazole is in the range of about 8% (w/w) to about 12% (w/w). In some embodiments, the amount of efinaconazole is about 10% (w/w). In some embodiments, the amount of efinaconazole is in the range of about 0.5% (w/w) to about 5% (w/w). In some embodiments, the amount of efinaconazole is about 2% (w/w).

In some embodiments, the amount of BHT is in the range of about 0.01% (w/w) to about 2% (w/w).

In some embodiments, the amount of EDTA or EDTA salt is in the range of about 0.0001% (w/w) to about 1.5% (w/w). In some embodiments, the amount of EDTA or EDTA salt is in the range of about 0.0001% (w/w) to about 0.0005% (w/w). In some embodiments, the composition is formulated as a solution. In some embodiments, the amount of EDTA or EDTA salt is about 0.00025% (w/w) and the amount of BHT is about 0.1% (w/w)

In some embodiments, the amount of EDTA or EDTA salt is in the range of about 0.01% (w/w) to about 1% (w/w). In some embodiments, the composition is formulated as a gel. In some embodiments, the amount of EDTA or EDTA salt is about 0.1% (w/w) and the amount of BHT is about 0.1% (w/w).

In some embodiments, the composition further comprises from about 0.01% citric acid (w/w) to about 1% citric acid (w/w). In some embodiments, the composition comprises from about 0.05% citric acid (w/w) to about 0.25% citric acid (w/w). In some embodiments, the composition comprises from about 0.075% citric acid (w/w) to about 0.15% citric acid (w/w).

In some embodiments, the color of the composition is determined by visual inspection. In some embodiments, the color is determined by assessing UV-vis absorbance values.

In some embodiments, after storage for at least one month at 65° C. the composition exhibits UV-vis absorbance values of 0.4 absorbance units (AU) or less at 400 nm; 0.1 AU or less at 500 nm; and/or 0.1 AU or less at 600 nm. In some embodiments, after storage for at least one month at 65° C. the composition exhibits UV-vis absorbance values of: 0.4 AU or less at 400 nm; 0.1 AU or less at 500 nm; and 0.1 AU or less at 600 nm.

In some embodiments, after storage for at least one month at 65° C. the composition exhibits UV-vis absorbance values of 0.2 AU or less at 400 nm; 0.03 AU or less at 500 nm; and/or (iii) 0.03 AU or less at 600 nm. In some embodiments, after storage for at least one month at 65° C. the composition exhibits UV-vis absorbance values of: 0.2 AU or less at 400 nm; 0.03 AU or less at 500 nm; and 0.03 AU or less at 600 nm.

In some embodiments, after storage for at least one month at 65° C. the composition exhibits UV-vis absorbance of 0.1 AU or less at 400 nm; 0.01 AU or less at 500 nm; and/or (iii) 0.01 AU or less at 600 nm. In some embodiments, after storage for at least one month at 65° C. the composition exhibits UV-vis absorbance values of: 0.1 AU or less at 400 nm; 0.01 AU or less at 500 nm; and (iii) 0.01 AU or less at 600 nm.

In some embodiments, the composition is a pharmaceutically acceptable formulation that is effectively absorbed in the treatment of the nail.

In a second aspect, the invention provides methods of treating or preventing a fungal infection. The methods include administering a therapeutically effective amount of a formulation of the invention to a patient in need of such treatment.

DETAILED DESCRIPTION OF THE INVENTION

I. Definitions

As used herein, the term "pharmaceutical composition" refers to a mixture containing a pharmaceutically active ingredient, such as efinaconazole, and one or more pharmaceutically acceptable excipients (antioxidants, preservatives, carriers, etc.). Compositions for topical administration are formulated as solutions, sprays, ointments, lotions, gels, shampoos, and the like. "Pharmaceutically acceptable" compositions are those in which substituent components such as carriers, diluents, and excipients are compatible with each other and with the active ingredient. Pharmaceutically acceptable compositions are frequently made with pharmaceutical-grade active agents and excipients. It will be understood that pharmaceutically acceptable compositions are not deleterious to the recipient thereof.

As used herein, the term "efinaconazole" refers to (2R, 3R)-2-(2,4-difluorophenyl)-3-(4-methylenepiperidine-1-yl)-1-(1H-1,2,4-triazole-1- yl)butane-2-ol, also known as KP-103, and pharmaceutically acceptable salts thereof.

As used herein, the term "absorbance" refers to the amount of visible or ultraviolet light that is absorbed by a compound or a mixture of compounds. Absorbance can be determined using a UV-visible spectrophotometer according to known techniques.

As used herein, the term "storage" refers to the holding of a composition under controlled or uncontrolled conditions for a period ranging from a few minutes to several months or longer. Storage conditions that can be controlled include, for example, temperature, humidity, and the level of light. In many cases storage of a pharmaceutical formulation is under industry acceptable standards and/or standards that are mandated by regulatory agencies, such as US FDA.

As used herein, the term "treating" refers to an indicia of success in the treatment or amelioration of a pathology, condition, or symptom, including any objective or subjective parameter such as abatement; remission; diminishing of symptoms or making the symptom, pathology or condition more tolerable to the patient; and decreasing the frequency or duration of the symptom or condition. The treatment or amelioration of symptoms can be based on any objective or subjective parameter, including, e.g., the result of a physical examination. "Prevention" of a disease or condition or "prophylaxis" means reducing the probability of onset of a condition or disease, delaying the time to onset of a disease or condition, reducing the duration of a subsequently arising indication, and/or reducing the severity of a subsequently arising condition by administration of a composition to a subject that currently does not have a disease or suffer from a condition. Prevention can include, but is not limited to, complete avoidance of the future occurrence (or recurrence) of a condition or disease. The invention provides both methods of treating and preventing fungal conditions in humans.

As used herein, the term "fungal infection" refers to the unwanted growth of a fungus on the skin or nails of a person or animal. Fungal infections are typically caused by fungi including *Candida albicans, Cryptococcus neoformans, Aspergillus fumigatus, Trichophyton mentagrophytes*, and the like. Compositions of the invention can be useful in the treatment of, e.g., onychomycosis and various tinea types of fungal infections, including tinea capitis and tinea pedis.

The terms "about" and "around," as used herein to modify a numerical value, indicate a close range surrounding that explicit value. If "X" were the value, "about X" or "around X" would indicate a value from 0.9X to 1.1X, and more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

II. Anti-Fungal Compositions

In a first aspect, the invention provides a composition containing from about 0.5% to about 15% efinaconazole by weight, butylated hydroxytoluene (BHT), and a salt of ethylenediaminetetraacetic acid (EDTA). The composition, if free of colorants (as will usually be the case), is colorless at initial formulation and, after a period of storage of at least three weeks, will be colorless or have a pale yellow color. A composition in the context of the invention is typically a liquid (e.g., a solution) or a semi-solid composition (e.g., a gel, ointment, lotion, cream, or other form).

The determination of the color of a composition can be made by any suitable method or combination of methods. It will be understood that the composition can be colorless or a have a color such as pale yellow, yellow, orange, amber, or brown. Frequently, compositions of the invention are initially formulated such that they are both colorless, in terms of color, and also transparent or clear, in terms of visible material in the composition. Preferred compositions will remain colorless and clear after storage for a period of time at relatively high temperatures (e.g., temperatures of at least about 40° C., at least about 45° C., at least about 55° C., or higher, such as about 65° C.). In one aspect, color determination can be made by visual inspection. Visual inspection may include independent validation by a number of pharmaceutical formulation scientists or other individuals (e.g., 2, 3, 4, 5, 10, 20, 30, 50, or even more individuals). Human visual inspection may be made by comparison against standard (reference) color samples that aid in the determination of color. In another aspect, inspection of the color can be made by use of a device that measures color by any suitable means, such as a colorimeter or by computer-based color assessment methods. In a particular aspect, the determination of color is made by UV/visual spectrum absorbance measurements, particularly where the UV-vis absorbance measurements have been standardized against compositions that have been determined to be good representatives of clear, pale yellow (or another pale color), and unacceptable colors (such as dark orange). In a more particular aspect, the invention provides such compositions where after storage for at least one month at 65° C. the composition exhibits one or more UV-vis absorbance values selected from the group consisting of: 0.4 absorbance units (AU) or less at 400 nm; 0.1 AU or less at 500 nm; and 0.1 AU or less at 600 nm.

Components

In preferred embodiments, the compositions contain from about 0.5% (w/w) to about 15% (w/w) efinaconazole [i.e., (2R,3R)-2-(2,4-difluorophenyl)-3-(4-methylenepiperidine-1-yl)-1-(1H-1,2,4-triazole-1-yl)butane-2-ol, also known as KP-103].

In some embodiments, the compositions of the invention contain from about 1% to about 12.5% efinaconazole by weight. The amount of efinaconazole can be any amount that is suitable for the purpose of the composition. Typically, the amount of efinaconazole is an amount that is capable of producing a therapeutic or prophylactic antifungal effect in a human patient. The amount of efinaconazole can vary with the nature of the composition, such as whether the composition is primarily comprised of polar components, non-polar components, or a mix thereof and/or the degree to which the efinaconazole API is soluble in the composition. The compositions can contain, for example, from about 1% to about 5% efinaconazole, such as where the composition primarily contains polar components and/or where the efinaconazole is relatively highly soluble in the composition. The composition can contain from about 5% to about 10% efinaconazole where the composition contains significantly more non-polar components and/or where the efinaconazole is relatively less soluble in the composition. In some embodiments, the invention provides compositions that contain from about 7.5% to about 10.0% efinaconazole, from about 10% to about 15%, from about 2% to about 8% efinaconazole, or from about 4% to about 6% efinaconazole. Other ranges of efinaconazole between about 0.5% and about 15% can be suitable, depending on the identities and quantities of the other components in the compositions. In some embodiments, the compositions contain about 0.5%, 0.75%, 0.8%, 0.9%, 1%, 1.25%, 1.5%, 1.75%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, or about 15% efinaconazole by weight.

The classification of components of a composition as either polar or non-polar can be determined by formulation scientists. In general, polar solvents will be miscible with water and miscible with non-polar solvents. Examples of polar components that are regularly found in pharmaceutical and other formulations include ethanol, propylene glycol, glycerin, triacetin, water, and isopropyl alcohol. Examples of non-polar components include capric/caprylic triglycerides, myristyl lactate, diisopropyl adipate, isopropyl myristate, and cyclomethicone.

Compositions of the invention contain butylated hydroxytoluene (BHT) in an amount that, in combination with the amount of EDTA in the composition, is capable of maintaining color stability of the efinaconazole composition such that after a period of three weeks, one month, or longer, even at relatively high temperatures (e.g., about 40° C., about 50° C., about 60° C., about 65° C., or higher) the composition maintains a colorless or pale yellow color, as determined by visual inspection, UV-visual spectrum data, or other suitable color measurement methods. The amount of BHT can vary with the amount of EDTA present, the amount of efinaconazole, and the nature of the composition and the other components of the composition. The compositions can contain, for example, from about 0.01% to about 2% BHT, from about 0.01% to about 1% BHT, from about 1% to about 2% BHT, from about 0.5% to about 1.5% BHT, or from about 0.75% to about 1.25% BHT. In some embodiments, the compositions contain about 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.00%, 1.05%, 1.10%, 1.15%, 1.20%, 1.25%, 1.30%, 1.35%, 1.40%, 1.45%, 1.50%, 1.55%, 1.60%, 1.65%, 1.70%, 1.75%, 1.80%, 1.85%, 1.90%, 1.95%, or about 2.00% BHT by weight.

Preferred compositions contain a salt of ethylenediaminetetraacetic acid (EDTA). The salt of ethylenediaminetetraacetic acid can be any suitable salt. In general, the salt will be one that is acceptable for pharmaceutical formulations and compatible with efinaconazole. Frequently used salts are the disodium and tetrasodium salts of ethylenediaminetetraacetic acid. The amount of EDTA, or a salt thereof, can be any amount that in combination with the amount of BHT provides a colorless composition on initial formulation and maintains a colorless to pale yellow formulation at relatively high temperatures (e.g., at least about 40, at least about 50, or at least about 60° C.) for periods of at least about 3 weeks (e.g., at least about 4 weeks, at least about 6 weeks, at least about 8 weeks, at least about 10 weeks, at least about 12 weeks, at least about 4 months, at least about 6 months, or longer). Typically compositions according to the invention will contain from about 0.0001% to about 1% EDTA, or a salt thereof. The amount of EDTA or EDTA salt used will vary depending on factors including the amount of efinaconazole, the amount of BHT, and the nature of the formulation. For example, in a gel formulation the amount of EDTA or EDTA salt used will typically be higher than the amount used in a solution. Also, the amount of EDTA or EDTA salt that is used in a non-aqueous formulation or low water content formulation can be lower than the amount of EDTA or EDTA salt that is used in a formulation with higher water content. Thus, in some embodiments, the amount of EDTA or EDTA salt in a composition of the invention is between about 0.1% and about 1% by weight (e.g., about 0.2%-1%, about 0.25-0.75%, about 0.3-0.8%, or about 0.4-0.7%, such as 0.15%, 0.35%, 0.45%, 0.5%, 0.6%, 0.7%, or 0.9%). Such amounts are useful in, e.g., gel compositions. In some embodiments, the amount of EDTA or EDTA salt is between about 0.004% and about 0.2%, such as about 0.175%, about 0.15%, about 0.125%, or about 0.1%.

The inventors also have surprisingly found that in certain formulations the amount of EDTA or EDTA salt can be in the range of only about 0.0001% to about 0.0005%, such as from about 0.0001% to about 0.00025%, from about 0.00025% to about 0.00050%, or from about 0.0002% to about 0.0004% EDTA or EDTA salt. In particular embodiments, the compositions contain about 0.00010%, 0.00012%, 0.00014%, 0.00016%, 0.00018%, 0.00020%, 0.00022%, 0.00024%, 0.00026%, 0.00028%, 0.00030%, 0.00032%, 0.00034%, 0.00036%, 0.00038%, 0.00040%, 0.00042%, 0.00044%, 0.00046%, 0.00048%, or about 0.00050% EDTA or EDTA salt by weight. In particular embodiments, the amount of EDTA or EDTA salt included in the composition is in the range of about 0.0001% (w/w) to about 0.0005% (w/w) (e.g., 0.0002% or 0.0004%) and the amount of BHT is in the range of about 0.01% (w/w) to about 2% (w/w) (e.g., 0.02%, 0.04%, 0.05%, 0.07%, 0.08%, 1.0%, 1.2%, 1.4%, 1.5%, 1.7%, or 1.9%).

In some exemplary embodiments, the invention provides compositions wherein the amount of EDTA or EDTA salt is in the range of about 0.0001% (w/w) to about 0.0005% (w/w) and the amount of BHT is in the range of about 0.01% (w/w) to about 2% (w/w).

In some exemplary embodiments, the invention provides compositions wherein the amount of EDTA or EDTA salt is in the range of about 0.0001% (w/w) to about 0.0003% (w/w) the amount of BHT is in the range of about 0.05% (w/w) to about 0.15%. In some exemplary embodiments, the invention provides compositions wherein the amount of EDTA or EDTA salt is in the range of about 0.1% to about 1.0% by weight (e.g., about 0.15% w/w to about 0.75% w/w), the amount of BHT is in the range of about 0.01% (w/w) to about 2% (w/w) (e.g., about 0.02% or 0.025% to about 1.0% or 1.5% w/w), and the amount of efinaconazole is the range of about 0.5% (w/w) to about 5% (w/w) (e.g., about 1%, about 2%, or about 3%).

In some exemplary embodiments, the invention provides compositions wherein the amount of EDTA or EDTA salt is about 0.00025% (w/w) and the amount of BHT is about 0.1% (w/w).

The compositions of the invention can contain a polar solvent, a non-polar solvent, or a mixture of the two. In some embodiments, the composition includes a polar solvent system containing propylene glycol, glycerin, and ethanol. In some embodiments, the composition includes a non-polar solvent system containing $C_{12-15}$ alkyl lactate, diisopropyl adipate, cyclomethicone, and ethanol.

Compositions of the invention can contain, and often will contain, citric acid. Particularly where the composition includes the polar solvent system, citric acid is also present because the inventors have further surprisingly found that the presence of citric acid also aids in maintaining color stability in such compositions as compared to compositions containing the non-polar solvent system wherein citric acid may not be required to maintain color stability (and as compared to compositions that include a polar solvent system and do not include citric acid). Even in compositions that include a non-polar solvent system, the inventors have found that the presence of citric acid as a stabilizer, chelating agent (chelator), anti-oxidant, and/or pH adjusting agent, or otherwise does not significantly detract from color stability in compositions containing the non-polar solvent system.

The amount of citric acid can be any amount that when combined with the EDTA and BHT either results in acceptable color stability, while usually also providing a detectable anti-oxidant effect, or that preferably enhances the color stability of the composition over the color stabilizing effects of BHT and EDTA alone. Compositions according to such aspects of the invention can contain, for example, from about 0.01% citric acid to about 1% citric acid by weight. The compositions can contain from about 0.02% to about 0.5% citric acid, from about 0.05% to about 1.5% citric acid, from about 0.08% to about 0.8% citric acid, or from about 0.085% to about 0.5%, 0.4%, 0.3%, or 0.1% citric acid. In some embodiments, the compositions contain about 0.05%, 0.06%, 0.07%, 0.08%, 0.09%, 0.10%, 0.12%, 0.15%, 0.17%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, or about 1.00% citric acid by weight. As for BHT and EDTA, ordinarily skilled formulation scientists will be capable of determining appropriate amounts of citric acid to include in any particular efinaconazole composition given the guidance provided here with respect to color stability.

In some embodiments, the composition contains: from about 0.5% to about 15% efinaconazole by weight, such as from about 0.75% to about 12% efinaconazole by weight (e.g., about 1-5% or about 5-10% efinaconazole by weight), from about 0.01% to about 2% BHT by weight (e.g., about 0.2% to about 1.5% BHT by weight), and from about 0.0001% to about 1.5% EDTA or EDTA salt by weight (e.g., about 0.0001% to about 0.0005% EDTA or EDTA salt by weight or about 0.1% to about 1.25% EDTA or EDTA salt by weight), and about 0.1% to about 1% citric acid by weight.

In some exemplary embodiments, the composition contains: from about 0.5% to about 15% efinaconazole by weight, from about 0.01% to about 2% BHT by weight, from about 0.0001% to about 0.0005% EDTA or EDTA salt by weight, and from about 0.1% to about 1% citric acid by weight.

In some exemplary embodiments, the composition contains from about 0.5% to about 15% efinaconazole by weight, about 0.1% BHT by weight, and about 0.00025% EDTA or EDTA salt by weight. In some embodiments, the composition further contains about 0.1% citric acid by weight.

In some exemplary embodiments, the composition contains from about 0.5% to about 15% efinaconazole by weight, about 0.1% BHT by weight, about 0.00025% EDTA or EDTA salt by weight, and about 0.1% citric acid by weight.

In some embodiments, the composition contains about 10% efinaconazole by weight. In some embodiments, the composition contains about 5% efinaconazole by weight. In some embodiments, the composition contains about 2% efinaconazole by weight.

Compositions can include additional components that are compatible with the efinaconazole, BHT, EDTA, and, if present, citric acid components of the composition, and that preferably do not materially affect the basic and novel properties of the inventive compositions, such as the color stability of the composition. Often compositions will include co-solvents, which can be non-polar or polar and/or volatile or non-volatile. Further components are described in detail below.

Composition Color

The compositions of the invention typically exhibit color stability over extended storage periods. The compositions can be stable for periods lasting from about two weeks to several months or even years (e.g., about one year, about two years, or even about three years, or longer, at room temperature storage). The compositions can be shelf-stable, for example, for at least a month, or at least 3 months, or at least 6 months, or at least 9 months, or at least a year at temperatures that are higher than room temperature (RT), such as at least about 35° C., at least about 45° C., at least about 50° C., at least about 55° C., at least about 60° C., or higher. The compositions can be stored at around room temperature (i.e., 25° C.), at around 40° C., at around 65° C., or at other suitable temperatures.

It will be appreciated by those of skill in the art that the stability of a composition can be readily assessed by eye, which is a method used often in the assessment of color stability of products such as pharmaceutical compositions. In some embodiments, discoloration can be quantified by recording a measurement, such as the UV-vis absorbance of a composition or a diluted sample of the composition, which provides a more quantitative measure of color stability. In cases where absorbance of UV/visible light is used to assess color stability, the absorbance can be recorded at any suitable wavelength and using any suitable device or method. Useful absorbance measurements for efinaconazole compositions can be recorded at 400 nm, 500 nm, or 600 nm. Other wavelengths can be used for measurement, depending on the particular composition being analyzed and the concentrations of the composition components. Compositions that do not exhibit discoloration remain colorless. Compositions that remain colorless over extended periods are particularly preferred. Typically, colorless compositions have UV-vis absorbance values below 0.1 absorbance units (AU) at 400 nm, below 0.01 AU at 500 nm, and below 0.01 AU at 600 nm. Certain acceptable compositions exhibit a slight change in color. Such composition may turn pale yellow during storage. Typically, pale yellow compositions have UV-vis absorbance values below 0.2 AU at 400 nm, below 0.1 AU at 500 nm, and below 0.1 AU at 600 nm. One of skill in the art will appreciate that colorless and pale yellow compositions can be identified by visual inspection without the use of UV-vis measurements.

As noted above, in some embodiments the determination of color stability is made using a device that can quantify the color of the composition after a time of storage as compared to its initial color and/or against standard ranges that reflect acceptable color (usually as compared to controls and run with two or more samples). Any suitable device and measurement system can be used. Typically, ultraviolet-visible (UV-vis) absorbance units (AUs) determined by a spectrophotometer or similar device can be determined for a composition and assessed against AU values that provide a range, number, and/or cutoff that is deemed to reflect acceptable color stability in a composition. The range, cutoff, and/or value can change with various factors such as the wavelength at which the measurement is taken. In some aspects, multiple measurements at different wavelengths are performed. In some aspects, only a single measurement at a single wavelength is performed. In one exemplary embodiment, after storage for at least one month at 65° C. the composition exhibits UV-vis absorbance values of: 0.4 absorbance units (AU) or less at 400 nm; 0.1 AU or less at 500 nm; and 0.1 AU or less at 600 nm.

The compositions exhibit certain UV-vis absorbance values after storage for at least one month at 65° C. In preferred embodiments, the composition exhibits one or more UV-vis absorbance values selected from: 0.4 AU or less at 400 nm; 0.1 AU or less at 500 nm; and 0.1 AU or less at 600 nm. In some embodiments, after storage for at least one month at 65° C. the composition exhibits UV-vis absorbance values of: 0.4 absorbance units (AU) or less at 400 nm; 0.1 AU or less at 500 nm; and 0.1 AU or less at 600 nm.

The UV-vis absorbance of a composition or sample of a composition at 400 nm can be, for example, from about 0.1 AU to about 0.2 AU, or from about 0.2 AU to about 0.4 AU. The UV-vis absorbance at 400 nm can be about 0.1, 0.15, 0.2, 0.25, 0.3, 0.35 or about 0.4 AU.

The UV-vis absorbance of a composition or sample of a composition at 500 nm can be, for example, from about 0.01 AU to about 0.05 AU, or from about 0.05 AU to about 0.1 AU. The UV-vis absorbance at 500 nm can be about 0.01, 0.02, 0.03, 0.04, 0.05, 0.06, 0.07, 0.08, 0.09 or about 0.1 AU.

The UV-vis absorbance of a composition or sample of a composition at 600 nm can be, for example, from about 0.01 AU to about 0.05 AU, or from about 0.05 AU to about 0.1 AU. The UV-vis absorbance at 600 nm can be about 0.01, 0.02, 0.03, 0.04, 0.05, 0.06, 0.07, 0.08, 0.09 or about 0.1 AU.

In some embodiments, after storage for at least one month at 65° C. the composition exhibits one or more UV-vis absorbance values selected from: 0.2 absorbance units (AU) or less at 400 nm, 0.03 AU or less at 500 nm, and (iii) 0.03 AU or less at 600 nm. In some embodiments, after storage for at least one month at 65° C. the composition exhibits UV-vis absorbance values of: 0.2 absorbance units (AU) or less at 400 nm; 0.03 AU or less at 500 nm; and 0.03 AU or less at 600 nm.

In some embodiments, after storage for at least one month at 65° C. the composition exhibits one or more UV-vis absorbance values selected from: 0.1 absorbance units (AU) or less at 400 nm, 0.01 AU or less at 500 nm, and (iii) 0.01 AU or less at 600 nm. In some embodiments, after storage for at least one month at 65° C. the composition exhibits UV-vis absorbance values of: 0.1 absorbance units (AU) or less at 400 nm, 0.01 AU or less at 500 nm, and (iii) 0.01 AU or less at 600 nm.

The absorbance values described herein can also be exhibited after storage for 6 weeks, or 8 weeks, or 3 months, or 6 months, or 1 year, or longer.

Discoloration (or a lack thereof) can also be assessed by comparing a UV-vis absorbance value for a composition after a period of storage to a UV-vis absorbance value for the composition before the period of storage. In some embodiments, for example, the absorbance of a sample of the composition at 400 nm after storage for a set period is not more than 5 times the absorbance of the sample at 400 nm before the set period. In some embodiments, the absorbance of a sample of the composition at 500 nm after storage for a set period is not more than 10 times the absorbance of the sample at 500 nm before the set period. In some embodiments, the absorbance of a sample of the composition at 600 nm after storage for a set period is not more than 5 times the absorbance of the sample at 600 nm before the set period. In some embodiments, a sample of the composition appears very light yellow after a set storage period. In some embodiments, a sample of the composition appears colorless after a set storage period.

A sample can be any portion of a composition that is held for storage and/or analysis. The sample can consist of a composition of the invention as described herein, or a composition that has been diluted or concentrated as necessary to facilitate analysis. The storage period can be any length of time suitable for assessing the effects of storage on the physical and/or chemical properties of a composition. In some embodiments, the storage period is at least 4 weeks long. In some embodiments, the storage is conducted at a temperature of from about 20° C. to about 8° C. In some embodiments, the storage is conducted at a temperature of about 65° C.

Formulations

In general, the compositions of the invention are formulated to be administered topically. The compositions can be formulated, for example, as solutions, sprays, ointments, lotions, gels, shampoos, and the like. The compositions can also be formulated according to U.S. Pat. No. 8,486,978, as well as according to U.S. Pat. Appl. Pub. Nos. 2009/0175810 and 2014/0228403, the entirety of which are incorporated herein by reference in their entirety. The compositions of the present invention, however, generally exhibit enhanced stability when compared to known formulations. In a preferred embodiment, the composition is formulated as a solution. In some embodiments, preferred components include volatile solvents, non-volatile solvents, and wetting agents.

Volatile solvents are compounds which have a measurable vapor pressure, and preferably are compounds that have a vapor pressure of greater than about 100 Pa at room temperature. Examples of volatile solvents include: acetone, 2-amino-2-methyl-1-propanol, 1,2-butanediol, 1,4-butanediol, 2-butanol, ethanol, ethyl acetate, n-heptane, isobutanol, isopropyl alcohol, 1-propanol, 2-propanol, and water.

Examples of suitable non-volatile solvents include, but are not limited to, squalane, dibutyl sebacate, isopropyl laurate, isopropyl myristate, isopropyl palmitate, isopropyl stearate, myristyl alcohol, oleyl alcohol, oleic acid, lauryl lactate, myristyl lactate, mixed C12-15 alkyl lactates, diisopropyl adipate, octyldodecanol, caproic acid, caprylic acid, capric acid, lauryl benzoate, myristyl benzoate, mixed C12-15 alkyl benzoates, benzyl benzoate, tridecyl neopentanoate, light mineral oil, mineral oil, alpha terpineol, diethylene glycol monoethyl ether, n-methylpyrrolidone, dimethyl sulfoxide, ethyl lactate, propylene glycol, hexylene glycol, glycerol (glycerin), benzyl alcohol and glycerol triacetate.

Useful wetting agents are chemical compounds that reduce the surface tension of liquid compositions and do not build viscosity. Any surfactant or group of surfactants that is suitable for dermatologic applications is suitable for the invention. Such surfactants may function as wetting agents in the compositions of the invention, and as emulsifiers or solubilizers. The surfactants may be nonionic, anionic, cationic, zwitterionic, amphoteric, or ampholytic surfactants.

In some embodiments, the wetting agent is a volatile silicone. Such volatile silicones include linear or cyclic polyorganosiloxane compounds of formula $[R^a SiOR^b]_n$, wherein n is less than or equal to 6, and $R^a$ and $R^b$ are independently selected alkyl groups. A volatile silicone has a measurable vapor pressure under ambient conditions. Examples of cyclic volatile silicones include polydimethylcyclosiloxanes, generally known as cyclomethicones (such as cyclopentasiloxane, cyclotetrasiloxane, decylmethylcyclopentasiloxane, and the like). Examples of linear volatile silicones include linear polysiloxanes (such as hexamethyldisiloxane, octamethyltrisiloxane, and the like).

In some embodiments, the invention provides a pharmaceutical composition for treatment of a disorder of the nail or nail bed comprising efinaconazole, EDTA or a salt thereof, BHT, and optionally citric acid as described above, and further comprising an alcohol, a volatile silicone, and one or more esters of the formula RCO—OR', wherein R and R' may be identical or different and each of R and R' represents a linear or branched chain of an alkyl, alkenyl, alkoxycarbonylalkyl, or alkoxycarbonyloxyalkyl radical having from 1 to 25 carbon atoms. In some embodiments, the volatile silicone is present in the composition at a concentration less than 25% w/w. In some embodiments, the concentration of volatile silicone is less than 15%. In some embodiments, the ratio of the alcohol to volatile silicone in the composition % w/w is at least 2:3. In some embodiments, the ratio of the alcohol to volatile silicone is at least 3:1. In certain embodiments, the composition does not form a film when topically applied to the surface of a nail. In certain embodiments, the composition is free of polymeric film forming compounds.

In some embodiments, the invention provides a pharmaceutical composition for treatment of a disorder of the nail or nail bed comprising efinaconazole, EDTA or a salt thereof, BHT, and optionally citric acid as described above, and further comprising:

alcohol—10% to 80% (w/w);
cyclomethicone—0.01% to less than 25% (w/w); and
diisopropyl adipate plus either or both of C12-15 alkyl lactate and isopropyl myristate—5% to 90% (w/w).

In some embodiments, the invention provides a pharmaceutical composition for treatment of a disorder of the nail or nail bed comprising efinaconazole, EDTA or a salt thereof, BHT, and optionally citric acid as described above, and further comprising:

alcohol—50% to 70% (w/w);
cyclomethicone—10% to 15% (w/w);
diisopropyl adipate—8% to 15% (w/w); and
either or both of C12-15 alkyl lactate and isopropyl myristate—8% to 15% (w/w).

In certain embodiments, the composition of the invention is free of polymeric film forming compounds and does not form a solid film or hard lacquer or shell when applied to the surface of a nail. Formation of a lacquer, shell, or film occurs by a process of solvent casting following evaporation of a volatile solvent which leaves behind the polymeric film former as a solid residue. Nail lacquers containing polymeric film formers are described, for example, in U.S. Pat. Nos. 4,957,730; 5,120,530; 5,264,206; 5,346,692; and 5,487,776; the entirety of which patents are incorporated herein by reference. Examples of polymeric film forming compounds include polymers and copolymers of polyvinyl acetate, polyvinylpyrrolidone, methacrylic acid, polyvinyl butyrals, polyvinyl acetals, and cellulose derivatives such as cellulose acetate phthalate, cellulose acetate butyrate, cellulose acetate propionate, cellulose nitrate, cellulose sulfate, ethylcellulose, and cellulose acetate. A polymeric film forming agent can be present in the composition of the invention, however, if it is present in an amount below that which will result in the formation of a film or lacquer following application of the composition to the surface of a nail. In some embodiments, the pharmaceutical composition further comprises a thickening agent such as an acrylate crosspolymer (e.g., acrylates/C10-30 alkyl acrylate crosspolymer; sold under tradenames including CARBOPOL 1342). Those of skill in the art will appreciate that acrylate crosspolymers used in the present invention break upon contact with the surface of the skin and nails and do not form a film, hard shell, or lacquer.

The composition of the invention can contain other components, such as preservatives, lubricants, humectants, moisture regulators, foaming agents, binders, pH regulators, osmotic pressure modifiers, emulsifiers, colors, aerosol propellants, fragrances, or odor maskers. Those of skill in the art are aware of the components that are useful for a chosen formulation. Such components are described in sources such as *Remington: The Science and Practice of Pharmacy*, 20$^{th}$ ed., 2000. Useful combinations for the compositions of the invention include water/propylene glycol/glycerin/ethanol, water/C$_{12-15}$ alkyl lactate/diisopropyl adipate/cyclomethicone/ethanol, and other mixtures.

Accordingly, some embodiments of the invention provide compositions formulated as solutions. In some embodiments, the composition contains one or more components selected from a volatile solvent, a non-volatile solvent, and a wetting agent. In some embodiments, the composition contains one or more components selected from water, propylene glycol, glycerin, and ethanol. In some embodiments, the composition contains one or more components selected from water, C$_{12-15}$ alkyl lactate, diisopropyl adipate, cyclomethicone, and ethanol.

III. Methods of Treatment

In another aspect, the invention provides methods for treating conditions of the skin or nails. The methods include topically administering a composition of the invention to a patient in need thereof. In general, the skin and nail conditions are caused by fungi including *Candida albicans, Cryptococcus neoformans, Aspergillus fumigatus, Trichophyton mentagrophytes*, and the like. Examples of skin and nail conditions include, but are not limited to, tinea pedis (athlete's foot), tinea capitis (scalp ringworm), onychomycosis (tinea unguium), tinea cruris (jock itch), tinea corporis (ringworm), and yeast infections.

Tinea pedis is a fungal infection of the feet caused by *Trichophyton rubrum* or *Trichophyton mentagrophytes*. Tinea pedis can occur on the heel, on the plantar region of the sole, and on or between the toes. Tinea capitis is an infection of the scalp caused by *Microsporum audouinii, Microsporum canis, Trichophyton tonsurans, Trichophyton violaceum, Trichophyton schoenlenii*, and the like. Onychomycosis is an infection of the nail or nail bed caused by *Trichophyton rubrum, Trichophyton interdigitale (Trichophyton mentagrophytes), Epidermophyton floccosum, Trichophyton violaceum, Microsporum gypseum, Trichophyton tonsurans, Trichophyton soudanense*, and *Candida* species.

According to the methods of the invention, the compositions are topically applied to the affected area (such as the feet, scalp, or hands) at least three times a week for a period of from about one week to about 12 weeks, or until the disappearance of the condition. In some embodiments, the composition is applied once daily for about one to twelve weeks. In some embodiments, the composition is applied twice daily for about one to twelve weeks. Other dosing regimens can be used in the methods of the invention, depending on the type of fungus causing the condition and the severity of the condition.

The following examples are intended to illustrate, but not to limit, the aspects of the invention described above.

IV. Examples

Figure 1:
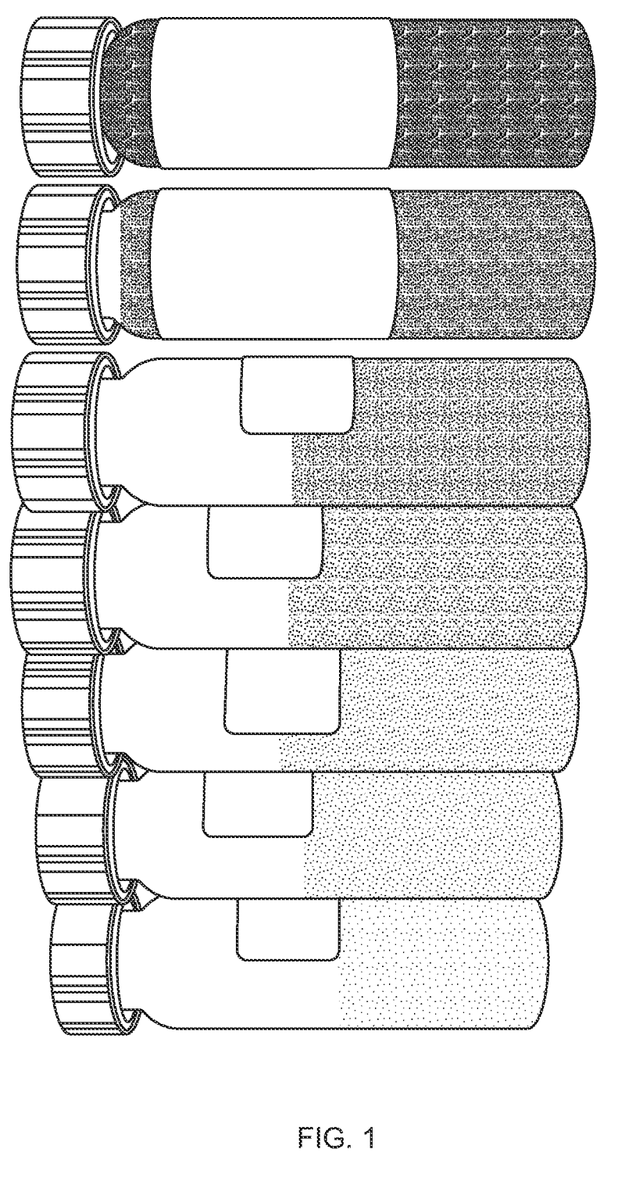
FIG. 1 shows efinaconazole solutions exhibiting varying levels of discoloration due to instability during storage.
Figure 2A:
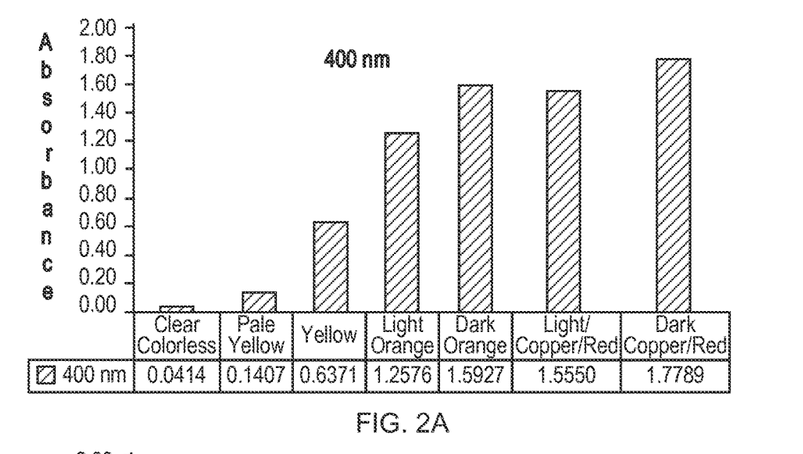
FIG. 2 shows UV-vis absorbance values for efinaconazole solutions exhibiting varying levels of discoloration, measured at (A) 400 nm, (B) 500 nm, and (C) 600 nm.
Figure 2B:
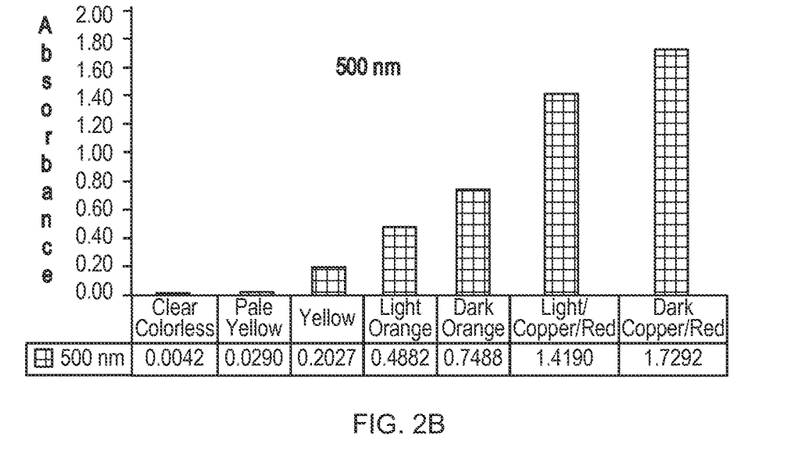
Figure 2C:
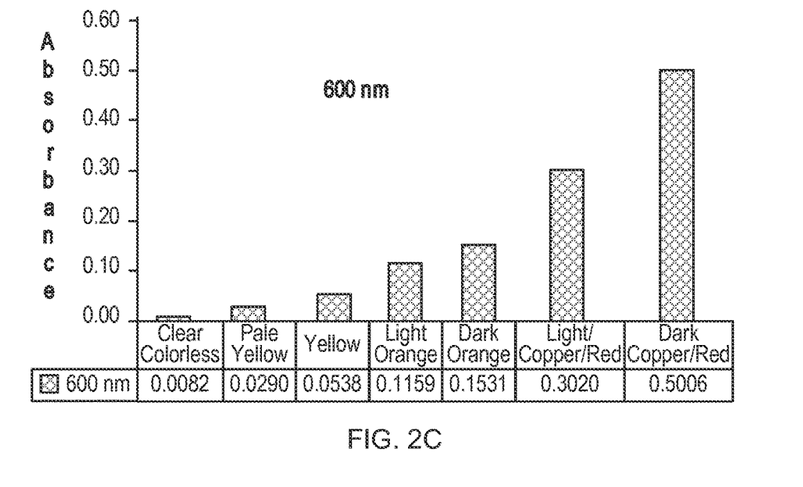

Solutions were prepared by combining efinaconazole and various solvents, resulting in mixtures to which antioxidants, hydroxy acids, and chelators were added as described below. Resulting solutions were clear and colorless when all components were first combined. The solutions were stored at 65° C. Over the storage period, certain solutions were observed to turn a pale yellow color. The color of certain solutions deepened to shades of yellow, light orange, dark orange, pink, copper, light red, and dark red. A photograph of solutions exhibiting various colors is shown in FIG. 1. UV-visible absorption spectra were recorded at various time points using a Varian Cary 50 Bio Spectrophotometer. Samples were scanned over 300 nm to 800 nm. Absorbance values were noted at 400, 500 and 600 nm. Based on the absorbance readings, the "time to failure" was determined using cutoff values of 0.1407 absorbance units (AU) at 400 nm, 0.0290 AU at 500 nm, and 0.0290 AU at 600 nm.

Examples 1-6, formulated as shown in Table 1, contained 10% efinaconazole by weight and various antioxidants in a water/alkyl lactate/diisopropyl adipate/cyclomethicone/ethanol solvent system. The results summarized in Table 2 show that UV absorbance values exceeded acceptable limits, reflecting unacceptable levels of color change in the formulation, within 2 weeks (Examples 1 and 5), and—in the case of propyl gallate—within only 4 days (Example 3).

TABLE 1

| Ingredients | 1 | 2 | 3 | 4 | 5 | 6 |
|---|---|---|---|---|---|---|
| EDTA disodium | 0.00025 | 0.00025 | | 0.00025 | 0.00025 | 0.00025 |
| Purified Water | 1.00 | 1.00 | | 1.00 | 1.00 | 1.00 |
| Citric Acid Anhydrous | 0.10 | 0.10 | | 0.10 | 0.10 | 0.10 |
| BHA | 0.10 | | | | | |
| Propyl Gallate | | 0.10 | 0.10 | | | |
| Ascorbic Acid | | | | 0.10 | | |
| Ascorbyl Palmitate | | | | | 0.10 | 0.20 |
| C12-15 Alkyl Lactate | 10.00 | 10.00 | 10.00 | 10.00 | 10.00 | 10.00 |
| Ceraphyl 230 (Diisopropyl Adipate) | 12.00 | 12.00 | 12.00 | 12.00 | 12.00 | 12.00 |
| Cyclomethicone | 13.00 | 13.00 | 13.00 | 13.00 | 13.00 | 13.00 |
| KP-103 | 10.00 | 10.00 | 10.00 | 10.00 | 10.00 | 10.00 |
| Alcohol, 190 Proof | Q.S. to 100 | Q.S. to 100 | Q.S. to 100 | Q.S. to 100 | Q.S. to 100 | Q.S. to 100 |

TABLE 2

| | DESCRIPTION | 1 month | Time to Failure | Absorbance 400 nm | 500 nm | 600 nm |
|---|---|---|---|---|---|---|
| 1 | citric acid, EDTA, BHA | Yellow | 2 wk | >0.1407 @ 400 nm | >0.0290 @ 500 nm | >0.0290 @ 600 nm |
| 2 | citric acid, EDTA, PROPYL GALLATE | Yellow | 1 wk | | | |
| 3 | propyl gallate | Orange/Red | 4 days | | | |
| 4 | citric acid, EDTA, ascorbic acid | Yellow | 1 wk | | | |
| 5 | citric acid, EDTA, ascorbyl palmitate | Yellow | 2 wk | | | |
| 6 | citric acid, EDTA, ascorbyl palmitate | Yellow | 1 wk | | | |

Examples 7-14, formulated as shown in Table 3, contained 10% efinaconazole by weight in the water/alkyl lactate/diisopropyl adipate/cyclomethicone/ethanol solvent system. The results summarized in Table 4 show that the compositions containing EDTA/BHT did not change significantly in color for over a month when stored at 65° C. (Examples 7 and 14). Citric acid can be included as an additional component in the EDTA/BHT formulations. Taken together, examples 7-14 show that BHT is a uniquely useful stabilizer for efinaconazole formulations, particularly when combined with EDTA and citric acid. The stability observed for formulations containing BHT was particularly unexpected given the instability observed for formulations containing BHA and propyl gallate.

TABLE 3

| Ingredients | 7 | 8 | 9 | 10 | 11 | 12 | 13 | 14 |
|---|---|---|---|---|---|---|---|---|
| EDTA disodium | 0.00025 | 0.00025 | | 0.00025 | | | | 0.00025 |
| Purified Water | 1.00 | 1.00 | | 1.00 | | 1.00 | 1.00 | 1.00 |
| Citric Acid Anhydrous | 0.10 | 0.10 | 0.10 | | | | 0.10 | |
| BHT | 0.10 | | | | 0.10 | | 0.10 | 0.10 |
| C12-15 Alkyl Lactate | 10.00 | 10.00 | 10.00 | 10.00 | 10.00 | 10.00 | 10.00 | 10.00 |
| Ceraphyl 230 (Diisopropyl Adipate) | 12.00 | 12.00 | 12.00 | 12.00 | 12.00 | 12.00 | 12.00 | 12.00 |
| Cyclomethicone | 13.00 | 13.00 | 13.00 | 13.00 | 13.00 | 13.00 | 13.00 | 13.00 |
| KP-103 | 10.00 | 10.00 | 10.00 | 10.00 | 10.00 | 10.00 | 10.00 | 10.00 |
| Alcohol, 190 Proof | Q.S. to 100 | Q.S. to 100 | Q.S. to 100 | Q.S. to 100 | Q.S. to 100 | Q.S. to 100 | Q.S. to 100 | Q.S. to 100 |

TABLE 4

| No | DESCRIPTION | 1 month | Time to Failure | Absorbance 400 nm | 500 nm | 600 nm |
|---|---|---|---|---|---|---|
| 7 | citric acid, EDTA, BHT | V. Light Yellow | >1 mo | 0.1407 | 0.029 | 0.029 |
| 8 | citric acid, EDTA | Yellow | 1 wk | >0.1407 @ 400 nm >0.0290 @ 500 nm >0.0290 @ 600 nm | | |
| 9 | citric acid | Yellow | 1 wk | | | |
| 10 | EDTA | Copper | 1 wk | | | |
| 11 | BHT | Copper | 1 wk | | | |
| 12 | No stabilizers | Orange | 1 wk | | | |
| 13 | BHT + citric acid | Yellow | 3 wk * | | | |
| 14 | BHT + EDTA | CC | >1 mo | 0.0414 | 0.0042 | 0.0082 |

Examples 15-19, formulated as shown in Table 5, contained 10% efinaconazole by weight and various acid components in the water/alkyl lactate/diisopropyl adipate/cyclomethicone/ethanol solvent system. The results summarized in Table 6 show that the citric acid/EDTA/BHT formulation remained clear and colorless for over a month when stored at 65° C. (Example 19). For the other acid components, absorbance values exceeded acceptable limits within 2 or 3 weeks. Formulations according to Example 19 are particularly useful for the treatment of onychomycosis.

TABLE 5

| Ingredients | 15 | 16 | 17 | 18 | 19 |
|---|---|---|---|---|---|
| EDTA disodium | 0.00025 | 0.00025 | 0.00025 | 0.00025 | 0.00025 |
| Purified Water | 1.00 | 1.00 | 1.00 | 1.00 | 1.00 |
| Citric Acid Anhydrous | | | | | 0.10 |
| Acetic Acid | 0.10 | | | | |
| Lactic Acid | | 0.10 | | | |
| Tartaric Acid | | | 0.10 | | |
| Salicylic Acid | | | | 0.10 | |
| BHT | 0.10 | 0.10 | 0.10 | 0.10 | 0.10 |
| C12-15 Alkyl Lactate | 10.00 | 10.00 | 10.00 | 10.00 | 10.00 |
| Ceraphyl 230 (Diisopropyl Adipate) | 12.00 | 12.00 | 12.00 | 12.00 | 12.00 |
| Cyclomethicone | 13.00 | 13.00 | 13.00 | 13.00 | 13.00 |
| KP-103 | 10.00 | 10.00 | 10.00 | 10.00 | 10.00 |
| Alcohol, 190 Proof | Q.S. to 100 | Q.S. to 100 | Q.S. to 100 | Q.S. to 100 | Q.S. to 100 |

TABLE 6

| No | DESCRIPTION | 1 month | Time to Failure | Absorbance 400 nm | 500 nm | 600 nm |
|---|---|---|---|---|---|---|
| 15 | EDTA, BHT, acetic acid | Yellow | 2 wk | >0.1407 @ 400 nm >0.0290 @ 500 nm >0.0290 @ 600 nm | | |
| 16 | EDTA, BHT, lactic acid | Yellow | 2 wk | | | |
| 17 | EDTA, BHT, tartaric acid | Light Yellow | 3 wk | | | |
| 18 | EDTA, BHT, salicylic acid | Light Yellow | 3 wk | | | |
| 19 | EDTA, BHT, citric acid | CC | >1 mo | 0.0414 | 0.0042 | 0.0082 |

Examples 20-26, formulated as shown in Table 7, contained 10% efinaconazole by weight in a second solvent system. Example 27 contained 5% efinaconazole. As shown in Table 8, absorbance for all of the samples except for Example 20 exceeded acceptable absorbance levels within 4 days to 3 weeks. Example 20, containing citric acid, EDTA, and BHT remained clear and colorless for over one month when stored at 65° C.

TABLE 7

| Ingredients | Example No. (% w/w) | | | | | | | |
|---|---|---|---|---|---|---|---|---|
| | 20 | 21 | 22 | 23 | 24 | 25 | 26 | 27 |
| EDTA disodium | 0.00025 | 0.00025 | | 0.00025 | | 0.00025 | | |
| Purified Water | 1.00 | 1.00 | | 1.00 | | 1.00 | | |
| Citric Acid Anhydrous | 0.10 | 0.10 | 0.10 | | 0.10 | | 0.10 | 0.10 |
| BHT | | 0.01 | 0.10 | 0.10 | | | | |
| Propylene Glycol | 34.40 | 34.50 | 35.00 | 34.50 | 35.00 | 34.50 | 35.00 | 37.95 |
| Glycerin | 27.20 | 27.20 | 27.40 | 27.20 | 27.50 | 27.30 | 27.50 | 28.45 |
| Vitamin E | | | | | | | | 0.05 |
| KP-103 | 10.00 | 10.00 | 10.00 | 10.00 | 10.00 | 10.00 | 10.00 | 5.00 |
| Alcohol, 190 Proof | Q.S. to 100 | Q.S. to 100 | Q.S. to 100 | Q.S. to 100 | Q.S. to 100 | Q.S. to 100 | Q.S. to 100 | Q.S. to 100 |

TABLE 8

| No | DESCRIPTION | 1 month | Time to Failure | Absorbance | | |
|---|---|---|---|---|---|---|
| | | | | 400 nm | 500 nm | 600 nm |
| 20 | CA, EDTA, BHT | V. Light Yellow | >1 mo | 0.1407 | 0.029 | 0.029 |
| 21 | citric acid, EDTA | Orange/Red | 4 days | >0.1407 @ 400 nm | | |
| 22 | citric acid, BHT | Orange/Red | 2 wk | >0.0290 @ 500 nm | | |
| 23 | EDTA, BHT | Light Copper | 3 wk | >0.0290 @ 600 nm | | |
| 24 | citric acid | Orange/Red | 4 days | | | |
| 25 | EDTA | Orange/Red | 1 wk | | | |
| 26 | BHT | Orange | 2 wk | | | |
| 27 | vitamin E, BHT | Pinkish/Red* | <2 wk | | | |

Examples 28-33, as shown in Table 9, contained 2% efinaconazole by weight in gel formulations. As shown in Table 9, most formulations containing BHT and EDTA remained clear and colorless for 8 weeks. Example 9, without citric acid, gained only a very light color between 4 and 8 weeks.

TABLE 9

| | Contents | | | Color after storage at 65° C. | | | | |
|---|---|---|---|---|---|---|---|---|
| No. | BHT (%/w/w) | EDTA (%/w/w) | Citric acid (% w/w) | Initial | 1 wk | 2 wk | 4 wk | 8 wk |
| 28 | 0.1 | 0.1 | 0.2 | CC | CC | CC | CC | CC |
| 29 | 0.0 | 0.1 | 0.2 | CC | Dark Yellow | Orange | Light Amber | Amber |
| 30 | 0.1 | 0.1 | 0.0 | CC | CC | CC | CC | Light Yellow |
| 31 | 0.0 | 0.0 | 0.0 | CC | Orange | Light Amber | Amber | Amber |
| 32 | 0.5 | 0.1 | 0.2 | CC | CC | CC | CC | CC |
| 33 | 0.1 | 0.1 | 0.5 | CC | Not determined | CC | CC (3 wks) | CC (7 wks) |

Examples 34-39, as shown in Table 10, contained 2% efinaconazole by weight in additional gel formulations. Color of certain formulations was assessed by visual observation and the results are presented in Table 11. The excipients described in these formulations, as with other formulations provided herein, can be replaced with other known formulations having similar functions to generate additional suitable formulations according to the invention, but typically the EDTA and citric acid elements are maintained, along with the efinaconazole API.

TABLE 10

| Component | Example No. (% w/w) | | | | | |
|---|---|---|---|---|---|---|
| | 34 | 35 | 36 | 37 | 38 | 39 |
| Efinaconazole | 2.00 | 2.00 | 2.00 | 2.00 | 2.00 | 2.00 |
| Propylene glycol | 20.00 | 20.00 | 20.00 | 20.00 | 20.00 | 20.00 |
| Alcohol, 190 proof | 8.00 | 8.00 | 8.00 | 8.00 | 8.00 | 8.00 |
| Diethylene glycol monoethyl ether | 20.00 | 20.00 | 20.00 | 20.00 | 20.00 | 20.00 |
| Hexylene glycol | 12.00 | 12.00 | 12.00 | 12.00 | 12.00 | 12.00 |
| Acrylates/C10-30 alkyl acrylate crosspolymer | 2.00 | 2.00 | 2.00 | 2.00 | 2.00 | 2.00 |
| Niacinamide | 2.00 | 2.00 | 2.00 | 2.00 | 2.00 | 2.00 |
| Butylated hydroxytoluene | 0.10 | — | 0.10 | — | 0.50 | 0.10 |
| Edetate disodium | 0.1 | 0.1 | 0.1 | — | 0.1 | 0.1 |

TABLE 10-continued

| Component | Example No. (% w/w) | | | | | |
|---|---|---|---|---|---|---|
| | 34 | 35 | 36 | 37 | 38 | 39 |
| Citric acid, anhydrous | 0.2 | 0.2 | — | — | 0.1 | 0.5 |
| Purified water | qs 100 | qs 100 | qs 100 | qs 100 | qs 100 | qs 100 |

| | GELS, 2% KP-103, Color development | | 65° C. | | | |
|---|---|---|---|---|---|---|
| | DESCRIPTION | Initial | 1 wk | 2 wk | 4 wk | 8 wk |
| 24 | 0.1 BHT + 0.1 ED + 0.2 CA | CC | CC | CC | CC | CC |
| 25 | NO BHT + 0.1 ED + 0.2 CA | CC | Dark Yellow | Orange | Light Amber | Amber |
| 26 | 0.1 BHT + 0.1 ED + NO CA | CC | CC | CC | CC | V. light yellow |
| 27 | NO STABILIZERS | CC | Orange | Light amber | Amber | Amber |
| 28 | 0.5 BHT + 0.1 ED + 0.2 CA | CC | CC | CC | CC | CC |
| 35 | 0.1 BHT + 0.1 ED + 0.5 CA | CC | Not Determined | CC | CC (3 wks) | CC (7 wks) |

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A composition comprising about 8% to about 12% efinaconazole by weight, water, C12-15 alkyl lactate, diisopropyl adipate, cyclomethicone, ethanol, butylated hydroxytoluene (BHT), a salt of ethylenediaminetetraacetic acid (EDTA), and citric acid,
    wherein the amount of BHT is in the range of about 0.01% (w/w) to about 2% (w/w),
    wherein the amount of the salt of EDTA is in the range of about 0.0001% (w/w) to about 1.5% (w/w),
    wherein the amount of citric acid is in the range of about 0.05% (w/w) to about 0.25% (w/w),
    wherein the composition is formulated as a solution, and
    wherein the amounts of BHT and the salt of EDTA are sufficient to ensure the composition is (i) colorless upon initial formulation and (ii) colorless or pale yellow after storage for three weeks at a temperature of about 40° C.

2. The composition of claim 1, wherein the amount of efinaconazole is about 10% (w/w).

3. The composition of claim 1, wherein the amount of the salt of EDTA is in the range of about 0.0001% (w/w) to about 0.0005% (w/w).

4. The composition of claim 3, wherein the amount of the salt of EDTA is about 0.00025% (w/w) and the amount of BHT is about 0.1% (w/w).

5. The composition of claim 1, wherein the amount of the salt of EDTA is in the range of about 0.01% (w/w) to about 1% (w/w).

6. The composition of claim 5, wherein the amount of the salt of EDTA is about 0.1% (w/w) and the amount of BHT is about 0.1% (w/w).

7. The composition of claim 1, wherein the composition comprises from about 0.075% citric acid (w/w) to about 0.15% citric acid (w/w).

8. The composition of claim 1, wherein the color of the composition is determined by visual inspection.

9. The composition of claim 1, wherein the color is determined by assessing UV-vis absorbance values.

10. The composition of claim 9, wherein after storage for one month at 65° C. the composition exhibits UV-vis absorbance values of 0.4 absorbance units (AU) or less at 400 nm; 0.1 AU or less at 500 nm; and/or 0.1 AU or less at 600 nm.

11. The composition of claim 1, wherein the composition is a pharmaceutically acceptable formulation that is effectively absorbed in the treatment of the nail.

12. The composition of claim 1, comprising:
    ethanol in an amount ranging from 50% to 70% by weight,
    cyclomethicone in an amount ranging from 10% to 15% by weight,
    diisopropyl adipate in an amount ranging from 8% to 15% by weight, and
    C12-15 alkyl lactate in an amount ranging from 8% to 15% by weight.

13. The composition of claim 12, wherein the amount of the salt of EDTA is about 0.00025% (w/w) and the amount of BHT is about 0.1% (w/w).

14. The composition of claim 12, wherein the amount of citric acid is in the range of about 0.075% (w/w) to about 0.15% (w/w).

15. The composition of claim 13, wherein the amount of citric acid is in the range of about 0.075% (w/w) to about 0.15% (w/w).

16. A method of treating a fungal infection comprising administering a therapeutically effective amount of a formulation according to claim 11 to a patient in need of such treatment.

* * * * *

UNITED STATES PATENT AND TRADEMARK OFFICE
CERTIFICATE OF CORRECTION

PATENT NO.       : 9,662,394 B2                                                  Page 1 of 1
APPLICATION NO. : 14/505379
DATED            : May 30, 2017
INVENTOR(S)      : Bhatt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 84 days.

Signed and Sealed this
Twenty-fifth Day of September, 2018

Andrei Iancu
*Director of the United States Patent and Trademark Office*